United States Patent [19]

Vaseen

[11] 4,150,956

[45] Apr. 24, 1979

[54] PRODUCING MEDICAL GRADE OXYGEN FOR HUMAN, ANIMAL, OR LABORATORY USE BY PARAMAGNETIC SEPARATION OF OXYGEN FROM AIR

[76] Inventor: Vesper A. Vaseen, 9840 W. 35th Ave., Wheatridge, Colo. 80033

[21] Appl. No.: 891,548

[22] Filed: Mar. 30, 1978

[51] Int. Cl.² .................................................. B01D 19/00
[52] U.S. Cl. .................................................. 55/48; 55/3; 55/49; 55/51; 55/68
[58] Field of Search ............................. 55/38–44, 55/3, 48, 49, 51, 53, 68, 100, 279; 422/4, 24, 40

[56] References Cited

U.S. PATENT DOCUMENTS

| | | | |
|---|---|---|---|
| 172,245 | 7/1929 | DeBaufre | 55/68 |
| 341,727 | 5/1886 | Cabell | 210/243 |
| 2,628,083 | 2/1953 | Rense | 55/279 |
| 3,762,133 | 10/1973 | Merriman et al. | 55/48 |
| 3,881,896 | 5/1975 | Roghmayr | 55/279 |
| 3,930,813 | 1/1976 | Gessner | 55/68 |
| 4,049,398 | 9/1977 | Vaseen | 55/3 |

FOREIGN PATENT DOCUMENTS 992854  5/1965  United Kingdom .................. 55/68

Primary Examiner—Bernard Nozick

[57] ABSTRACT

The aeration of specific inert, nonmagnetic liquids, under superatmospheric pressure, and ambient temperature, increases both the oxygen and nitrogen solubility of the liquid. Filtered, sterilized air, within a controlled temperature range is dissolved under superatmospheric pressure in the nonmagnetic liquid. The liquid pregnant with both oxygen and nitrogen is then passed through a high intensity electromagnet which paramagnetically separates the oxygen from the liquid. The collected oxygen gas is pressurized for storage and later use, or used as produced. The oxygen stripped nonmagnetic liquid, still pregnant with nonparamagnetic nitrogen is reduced to sub or atmospheric pressure which releases the nitrogen gas to atmosphere. The gases stripped nonmagnetic liquid is then returned for recycle use.

7 Claims, 1 Drawing Figure

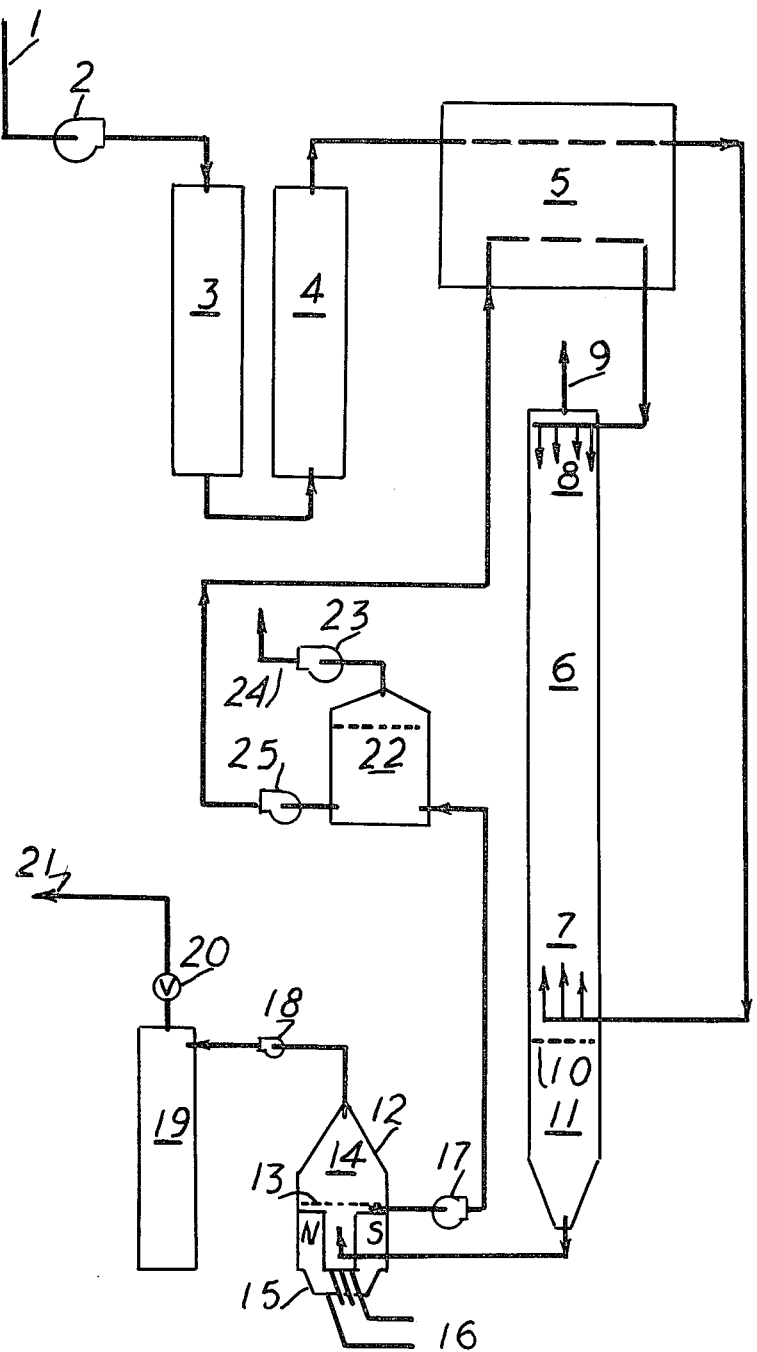

PRODUCING MEDICAL GRADE OXYGEN FOR HUMAN, ANIMAL, OR LABORATORY USE BY PARAMAGNETIC SEPARATION OF OXYGEN FROM AIR

BACKGROUND OF THE INVENTION

A combination of two physical factors makes it possible to collect dissolved oxygen from a liquid in a manner applicable to commercial production of gaseous oxygen. These two factors are the affinity of specific, inert, nonmagnetic liquids to dissolve more air, and thus oxygen, than some other liquids; and the fact that oxygen molecules are paramagnetic and can be magnetically removed from these specific liquids as gaseous oxygen. Nitrogen being practically nonparamagnetic remains as a dissolved gas in the liquid. It is then stripped by pressure reduction or heat and the liquid recovered for reuse.

The inert nonmagnetic liquid selected is one which is nonmiscible with water. This factor eliminates the necessity to dry air prior dissolving it in the liquid.

The use of medical oxygen by individuals, specially in their homes, offices, laboratories, etc., requires the availability of spare oxygen bottles, which introduces a factor of vulnerability to both storage and available supply.

The ability of an individual in need of pure oxygen to manufacture it from semi portable or portable equipment, from a closed cycle process, by the simple expedient of turning on the equipment by activating an electrical switch using household current characteristics is now possible with this invention.

The invention expands on the simple function of manufacturing paramagnetic oxygen as outlined prior to; by creating a complete cycle of operating equipment which combined together, accomplish the production of medical grade oxygen for immediate or later use, by the patient, if desired, at any place electrical energy is available to operate the equipment.

The invention utilizes the process steps of filtering air to eliminate particulates; sterilize the air to eliminate live virus; bacteria or other hazardous organisms to the buoy; adjust the temperature of the particulate free, sterilized air, dissolve the air in the absorber liquid; paramagnetically remove the gaseous oxygen from the absorber liquid; deliver the collected medical grade oxygen to the user or store it under pressure for later use; strip the absorber liquid of nitrogen gas; and return the absorber liquid to the absorber vessel.

DESCRIPTION OF PRIOR ART

Principal production of oxygen has been the cumbersome equipment and process of gases separation by low temperature, minus 200° F., methods of liquefaction and distillation (rectification) of the liquid. Pure oxygen is difficult by this method as air contains nine principal components, each of which have very low boiling points, several of which are very close together.

Electrolytic decomposition of water to produce pure oxygen and hydrogen, is a viable method, but is both expensive of operation as well as hazardous due to explosive hydrogen gas evolved.

Chemical or physical breakdown of oxides by chemical or heat action are also viable commercial means of producing oxygen, but they do not lend themselves to production of medical grade oxygen at point of use.

REFERENCES

U.S. Pat. No.:

| | | | |
|---|---|---|---|
| 341,727 | 5/1886 | Cabell | 210/243 |
| 1,056,043 | 3/1913 | Morrison | 55/3 |
| 1,056,244 | 3/1913 | Wiley | 55/68 |
| 1,722,458 | 7/1929 | DeBaufre | 55/68 |
| 3,177,633 | 4/1965 | McDonald, Jr. | 55/3 |
| 3,762,133 | 10/1973 | Merriman et al. | 55/08 |
| 4,049,398 | 9/1977 | Vaseen | 55/3 |

SUMMARY OF INVENTION

Ambient air is caused to pass through a mechanical filter, preferably of the type which has replaceable cartridges. The compressor or blower which causes the air to pass through the filter is preferably, used to pressurize the air to the same pressure as is designed into the absorber vessel, and total system.

The air is filtered to remove particulates, preferably including 100% removal of all particulates greater than 0.5 microns.

Filtered air is then sterilized prior to its introduction into the absorber liquid in the absorber vessel. Sterilization can be by heat or radiation. Preferably a means such as ultraviolet radiation is used. Heat is destructive of the solubility efficiency of the absorber liquid; and prior to the absorber vessel a temperature adjustment is made for this purpose. Sterilization by heat increases the load on the temperature adjustment apparatus.

The filtered, sterilized, temperature adjusted air is then commingled with the absorber liquid in the absorber vessel. Commingling is preferably done under superatmospheric pressure in order to increase the quantity of air dissolved per volume of absorber liquid used. The commingling is accomplished in many ways, by various methods, but preferably by the production of small bubbles of air it is introduced to the absorber liquid, such as through a venturi mixer. Air which is not dissolved in the absorber liquid is preferably recycled back from the top of the absorber vessel to the injection nozzel or system.

Absorber liquid selected has the following general specifications:

1. Boiling point several times that of water.
2. Specific gravity either greater or less than water—for easy separation.
3. Practically nonvolatile.
4. Critical temperature—several times that of boiling water.
5. Nonmiscible with water.
6. Nontoxic to bio-organisms.
7. Stable physical/chemical characteristics at ambient as well as elevated temperatures (for instance 600° F.), and at superatmospheric pressure (at least 40 atmospheres); and at subatmospheric pressure (at least minus 5 atmospheres).
8. Nonbiodegradable.
9. Nonoxidizable—even with ozone
10. A dielectric
11. Nonmagnetic
12. An affinity for dissolving air
13. Reusable for numerous cycles.
14. Nonflammable.

Two of the families of liquids which meet these specifications are the silicone liquids or polyorganosiloxanes; and the halogenated hydrocarbons, specially the halogen saturated compounds with one or more florine atoms.

The system of aeration of the inert liquid and the removal of the dissolved oxygen can both be operated as a pressure control system or either the aeration and-/or the paramagnetic oxygen collection system by operated independently as a pressure (vacuum) control system.

The aeration of the nonmagnetic inert liquid under positive pressure increases both the oxygen and nitrogen solubility of the fluid; which necessarily requires the paramagnetic removal of magnetic oxygen in the electromagnet be kept under at least equal pressure to retain the dissolved nitrogen in solution until the oxygen has been paramagnetically removed, thus preventing nitrogen contamination of the collected oxygen gas.

Negative pressure of reduction from a positive pressure, at the electromagnet will when following the electromagnet, release the dissolved nitrogen for either collection or dissipation back to atmosphere.

Heat is generated at the electromagnet due to the necessity to highly saturate the iron core of the magnet with gauss forces. This heat is removed by the specific heat factor of the nonmagnetic inert liquid.

Weak magnetic materials known as members of the paramagnetic group, are not very susceptible to an applied magnetic field. Paramagnetic materials rarely become saturated so their degree of magnetization continues to increase as the applied magnetic field gets stronger.

When a uniform magnetic field is applied to a magnetized particle, the forces acting on the two poles of the particle are equal and opposite. When an applied magnetic field differs in intensity at the two extremes of a particle, then a net differential magentic force acts on the particle. The net force exerted on a magnetized particle by a magnetic field is proportional to: (1) the intensity of the magnetization the field has induced in the particle; (2) the volume of the particle; (3) the gradient of the exerted magnetic field; that is, the difference between the intensity of the field at one end of the particle; and the intensity of the field at the other end of the particle.

Paramagnetic materials require a magnetic field of great enough intensity as to cause magnetization of the particles, as well as sufficient gauss flux gradient as to cause the particles to orient with temporary north and south poles.

The oxygen molecules when in the presence in an intense magnetic field orient as polar molecules with a north and a south pole. Due to the creation of a gradient field the oxygen molecules are then oriented and by nature of the differential forces on the poles created by the gradient field attracted north polar oriented to the south magnetic pole and vice versa. Molecular oxygen collected at each pole combine as they accumulate to form bubbles of free oxygen gas as the concentration exceeds the solubility of the liquid for absorbed oxygen and release themselves from the liquid as bubbles of oxygen to be collected for removal to storage and/or use.

The air (oxygen) saturated nonmagetic, inert liquid is passed thru the two magnetic poles, north and south, of an electromagnetic in a quantity and with a velocity which provide the time required, permit the absorbed oxygen molecules in the presence of gauss forces sufficient to cause paramagnetic magnetization of the oxygen molecules, to be magnetically attracted to the two poles, north and south, and at or near the magnetic pole surfaces, exceed the solubility ability of the liquid to retain the oxygen as absorbed oxygen, and thus release it as bubbles of free collective molecules, to the oxygen gas collector also installed at or near the surface of the liquid and between the two magnetic poles of the electromagnet.

In a pressurized system the oxygen gas can be removed at atmosphere pressure to storage, thence compression and use; or in an atmospheric system be collected by a vacuum (negative pressure) system to storage, compression and use.

The imposing of very high intensity gauss forces at the electromagnetic to induce paramagnetizm reactions on the absorbed oxygen molecules will produce heat. This heat can be designed to be collected by the specific heat capacity of the nonmagnetic inert liquid, to assist in nitrogen stripping or it can be externally removed by circulating other fluid and heat exchanger transfer from the magnet core iron to the auxiliary fluid.

Collection of the released effervescent oxygen is enhanced by the lowering of the pressure at the environmental space over the poles of the magnet.

The gaseous oxygen is collected by the vacuum pump which reduces the pressure adjacent to the magnetic poles, and slightly reduces the environmental space pressure receiving the effervescent oxygen; and sent to a storage vessel, also under pressure, or through a pressure control/rate of flow control apparatus to the user.

The oxygen stripped absorber liquid is removed from the vicinity of the magnetic poles, then its pressure reduced to atmospheric or subatmospheric, thus so decreasing the solubility of the absorber liquid the liquid pregnant with nonmagnetic nitrogen, releases it by effervescence to atmosphere.

The absorber liquid is then returned to the absorber vessel for recycle use. A filter for the liquid is optional in the flow sheet to separate out any particulates which might occur in the equipment and apparatus cycle. Water vapor which escaped capture or has been carried into the absorber with the air, being nonmiscible with the absorber liquid is also separated out at this time. The heat of magnetic separation of the oxygen, produced in the paramagnetic separator, is removed by a temperature adjustment heat exchanger, then the absorber liquid returned to the absorber vessel for recycle use.

PREFERRED EMBODIMENTS

It is the intention of this invention to teach the art and science of producing oxygen of medical grade for use by; individuals, human or animal, with a medical or other need to breath pure oxygen or oxygen enriched air; or for laboratory work requiring medical grade oxygen.

For example this explanation of the art and science will concern itself with the requirements of a semiportable self contained unit, which preferably will provide in excess of one hundred percent of the oxygen requirements of a large adult male. The selection of a large adult male as the preferred size will therefore produce more than sufficient oxygen for females or children.

A large adult male breaths approximately 500 cc each tidal cycle (breath in and out). The following table illustrates the weight of oxygen and nitrogen (air), per each tidal cycle. Preferably not less than this minimum amount of oxygen is produced.

| Ambient Temperature | | Grams Per Each 500 CC Air | | |
|---|---|---|---|---|
| °C. | °F. | Air | Nitrogen | Oxygen |
| 21.11 | 70 | 0.6013 | 0.4621 | 0.1392 |
| 23.89 | 75 | 0.5958 | 0.4579 | 0.1379 |
| 26.67 | 80 | 0.5902 | 0.4536 | 0.1366 |
| 29.44 | 85 | 0.5845 | 0.4492 | 0.1353 |

Medical use of past history provides patients use of oxygen gas at a range of two (2) to eight (8) liters per minute at atmospheric pressure.

Patient use of oxygen ranges between 0.55 grams to 2.20 grams per minute. Preferably the production of oxygen is two grams per minute.

Air is supplied to the system at preferably 70° F. (21.11° C.) at a rate which will deliver to the absorber liquid not less than two (2) grams of oxygen per minute. The air is preferably provided by a variance capacity system which is adjustable from 0 to 2.5 grams per minute.

The air is moved from ambient environment through the system by a pump, compressor, or blower. Those versed in the art and science of moving air will have no difficulty selecting suitable equipment for this function. It need only be remembered the equipment must be of type and construction as to not introduce oil or other deletarious or organic substances into the system. The pressure selected is preferably the pressure at which the air and the absorber liquid will be commingled in the absorber vessel. Although any pressure can be selected from atmospheric up to the critical pressure of the selected liquid, preferably for residential, hospital, or laboratory use a lower pressure is selected, for example ten (10) atmospheres.

Filtered air passes through a sterilizer to eliminate any possibility of contaminated air and thus contaminated oxygen reaching the patient. Sterilization is achieved by heating the air to preferably at least 160° F. (71.11° C.) for not less than 30 seconds, or at higher temperatures with less retention time.

Those versed in the art and science of pasturization will have no difficulty in selecting both standard equipment and temperature/time combinations which will satisfactorily pasturize the influent air.

Sterilization is also achieved as an alternate, by ultraviolet light or other high frequency, radiant energy radiation. Those versed in the art and science of radiation sterilization and pasturization will have no difficulty selecting both equipment and type radiation which will sterilize the air passed through it.

Preferably the air introduced into the absorber be at ambient for example 70° F. (21.11° C.) or lower temperature, therefore, a temperature adjustment apparatus is used between the sterilizer and the dissolver to make this temperature adjustment. Preferably the apparatus be a heat exchanger type so as to insure there not be contamination of the previously sterilized air. Those versed in the art and science of "Heat Flow" will have no difficulty selecting standard equipment to provide this function.

The dissolver is preferably a closed, pressurized vessel which efficiently commingles the air, as introduced, to provide very tiny bubbles to the absorber liquid; and a maximum of surface area of liquid; such as through a venturi type mixer. Excess undissolved air is preferably collected over the liquid surface of the absorber vessel, and recycled back to the air injection apparatus into the absorber vessel. The absorber liquid, also preferably at 70° F. (21.11° C.) is injected into the absorber vessel at the same pressure as the air, although any pressure from ambient to 100 atmospheres is acceptable, preferably at ten (10) atmospheres. Absorption of the air by the absorber liquid is complete in a few seconds, but in order to provide a reservoir of air saturated liquid to the paramagnetic oxygen separator, the vessel preferably retains two minutes supply of liquid, or 2.00 liters.

The absorber liquid pregnant with dissolved air is then passed to the paramagnetic separator apparatus, and discharged, preferably at ten (10) atmospheres through the poles of high intensity magnets. The oxygen being magnetic is collected at the magnets poles, where it supersaturates the volume of liquid containing it, and bubbles off or effervesces out of solution. The pressure is slightly reduced adjacent to the magnets poles, for example to 9.5 atmospheres, which permits the effervescent oxygen to be collected and removed from the paramagnetic separator apparatus. Oxygen is removed at the rate of preferably 2 grams per minute to an oxygen storage vessel or through a pressure reduction and control valve to direct use. Preferably oxygen is removed in direct proportion to the air quantity supplied the system.

The absorber liquid still pregnant with nitrogen is removed from the paramagnetic oxygen apparatus to a stripper vessel. The stripper vessel preferably is one which reduces the pressure on the absorber liquid to atmospheric or subatmospheric. The nitrogen gas absorbed in the absorber liquid at for example, ten (10) atmospheres, is at atmospheric or subatmospheric supersaturated and is thus released by effervescence to atmosphere or recovery. The released nitrogen gas is used to purge the environment adjacent to the other apparatus to provide it an inert atmosphere. Those familiar with degasification of liquids will have no problem in selecting equipment and apparatus to accomplish this function. For example the production of each 2 grams of oxygen per minute will require stripping equipment to release 6.639 grams of nitrogen per minute.

The nitrogen gas may also be heat stripped from the absorber liquid, but preferably is accomplished by differential pressure.

The gases free absorber liquid is now ready for return to the dissolver apparatus for reuse. Prior to return it is preferably, filtered to remove any particulates which may have to be picked up through the system, and the temperature readjusted by heat exchanger to preferably 70° F. (21.11° C.).

Thus it may be seen that medical grade, sterile, oxygen for human, animal, or laboratory use may be manufactured in compact, even portable, facilities and within closed circuits by paramagnetically separating oxygen from nitrogen, both of which, as air, have been dissolved in an inert, nonmagnetic liquid. While the present invention has been described in a certain degree of particularity, it is understood that the present disclosure has been made. By way of example and that changes in details of structures and arrangement of structures may be made without departing from the spirit thereof.

What is claimed is:

1. A method of manufacturing or producing medical grade oxygen for human, animal, or laboratory use by paramagnetic separation of oxygen from air comprising the steps of:

compressing or pumping ambient air, filtering said air,
sterilizing said air,
adjusting the temperature of said air,
dissolving said air in an inert, and non-magnetic, nontoxic, nonvolatile, absorber liquid,
passing the absorber liquid containing the dissolved air between the poles of a high intensity magnet to thereby evolve oxygen magnetically collecting the dissolved oxygen at the poles of the high intensity magnet,
collecting the effervescent, released oxygen,
transferring the produced oxygen to storage, or
transferring the produced oxygen to direct use,
controlling the pressure of oxygen released to use,
stripping the absorber liquid after oxygen removal of dissolved nitrogen,
filtering the absorber liquid of particulates collected in the system,
adjusting the temperature of the absorber liquid prior to injection back into the dissolving step,
recycling the absorber liquid to the dissolving step,
recycling non dissolved air from the dissolving step back to and with the air injection in the dissolving step.

2. The method of claim 1 wherein the temperature of the system preferably operates between 32° F. (0° C.) and 220° C. (104.44° C.).

3. The method of claim 1 wherein the pressure of the system preferably operates between a subatmospheric pressure of minus five (5) atmospheres and superatmospheric pressure of one hundred (100) atmospheres.

4. The method of claim 1 wherein the air is filtered free of particulates preferably ranging from 0.01 micron to 2,000 micron in diameter.

5. The method of claim 1 wherein the air in the system is sterilized by heat or irradiation, or both.

6. The method of claim 1 wherein effervescence of the gaseous oxygen at the magnet poles is assisted in its release from the nonmagnetic liquid by reduction in the operating pressure of the liquid between the poles; preferably from (0.01) one hundredth of an atmosphere to five (5) atmospheres.

7. The method of claim 1 wherein the absorber liquid is temperature adjusted for recycle use; from 32° F. (0° C.) to 212° F. (100° C.).

* * * * *